United States Patent [19]

Ego et al.

[11] Patent Number: 5,547,645

[45] Date of Patent: Aug. 20, 1996

[54] APPARATUS FOR DISSOLVING AN ADJUSTING AGENT OF A DIALYTIC SOLUTION

[75] Inventors: Tomomichi Ego; Hiroshi Kinoshita, both of Tokyo, Japan

[73] Assignee: Nikkiso Co., Ltd., Tokyo, Japan

[21] Appl. No.: 735,302

[22] Filed: Jul. 24, 1991

[30] Foreign Application Priority Data

Jul. 30, 1990 [JP] Japan .................................. 2-199128

[51] Int. Cl.[6] .............................. B01F 1/00; B01F 15/02
[52] U.S. Cl. ...................... 422/264; 422/281; 137/268; 222/64; 222/325; 366/136
[58] Field of Search .................................. 422/263, 264, 422/266, 281; 137/268, 88; 366/154, 136; 222/148, 64, 325

[56] References Cited

U.S. PATENT DOCUMENTS

| | | | |
|---|---|---|---|
| 2,762,527 | 9/1956 | Manley | 422/266 |
| 4,197,942 | 4/1980 | Gacki et al. | 366/154 |
| 4,515,482 | 5/1985 | Schadewald | 366/136 |
| 4,580,699 | 4/1986 | Black et al. | 222/64 |
| 4,664,891 | 5/1987 | Consentino et al. | 422/269 |
| 4,732,297 | 3/1988 | Schroeder, Jr. | 222/64 |

Primary Examiner—Robert J. Warden
Assistant Examiner—E. Leigh Dawson
Attorney, Agent, or Firm—Young & Thompson

[57] ABSTRACT

An apparatus for dissolving an adjusting agent of a dialytic solution according to the invention includes a vessel containing sealingly a constant quantity of a powdery or granular solid adjusting agent of a dialytic solution, a feeding means for supplying a fluid for dissolving the adjusting agent in said vessel, and a dissolving tank for mixing and dissolving the adjusting agent with the fluid and for storing the mixed solution.

2 Claims, 4 Drawing Sheets and, much work is necessary for disposal of the remaining solution, a washing procedure of the tank and other steps even after dialysis.

APPARATUS FOR DISSOLVING AN ADJUSTING AGENT OF A DIALYTIC SOLUTION

FIELD OF THE INVENTION

This invention relates to an apparatus for dissolving an adjusting agent of a dialytic solution (hereinafter, referred to as "an adjusting agent") to be used for hemo-dialysis. More particularly, the invention relates to an apparatus for dissolving an adjusting agent, which is able to dissolve the solid adjusting agent hygienically with reduced labor.

BACKGROUND OF THE INVENTION

An adjusting agent of a dialytic solution (hereinafter, referred to merely as "an adjusting agent") is now commercially available in the form of a concentrated solution, as well as a powdery or granular solid agent and may be optionally dissolved in diluting water for adjusting its concentration to be useful for a dialytic solution.

As this type of the dialytic solution, there have been employed bicarbonate or acetate systems. For the bicarbonate system, two types of the adjusting agents, namely one without sodium bicarbonate (hereinafter, referred to as "A agent") and the other sodium bicarbonate per se (hereinafter, referred to as "B agent"), are used. As the solid adjusting agent, there has been mainly utilized the B agent which is the adjusting agent for the bicarbonate system.

When the dialytic solution is prepared from the solid adjusting agent, at first the adjusting agent is generally dissolved in water to form a concentrated solution which is then supplied to an adjusting unit for mixing with additional water to adjust the dialytic solution.

In the adjusting unit for feeding the dialytic solution to a plurality of dialyzers, in order to dissolve and mix the solid adjusting agent in water a conventional procedure has been employed in which a required quantity of water to prepare the concentrated solution necessary for every simultaneous dialysis is stored in a given tank while a plurality of containers (in most cases a transparent bag) each containing the solid adjusting agent is opened by hand, and then the adjusting agent is dosed from all of the containers into a tank for dissolving the same in water by means of mechanical agitation using an agitator (an agitating blade) or the like provided in the tank.

Usually, such dissolving and mixing operation is not carried out in a sanitary atmosphere such as a clean room, and consequently bacteria and dust in the air often come into contact with the adjusting agent and the concentrated solution after dissolution on the one hand, while the opening and dosing operation of the containers should be carried out manually, resulting in many chances of contact with operator's hands on the other hand, which presents a hygienic problem. Further, it is not desirable to leave the concentrated solution for a long period of time after dissolution or to dissolve the agent on the day before use in dialysis and leave it, because of a hygienic problem and possibility of change in concentration of the solution as well. Particularly, the concentrated solution of sodium bicarbonate is relatively unstable and has a short shelf life, so that it should be dissolved and consumed at the time of dialysis. For this reason, the dissolving and mixing operation must be carried out in the busy time before starting dialysis, resulting in a heavy load for an operator engaging in dialysis. Further, much work is necessary for disposal of the remaining In view of the above, there has hitherto been proposed a continuous saving apparatus for dissolving sodium bicarbonate continuously and automatically (Japanese Patent Publication 1-55893), in which sodium bicarbonate is supplied by a powder-feeding means such as a feeder of powder while water is supplied by a water-feeding means respectively to an agitation tank, and the powder-feeding and/or the water-feeding means may be controlled depending on a concentration of a solution after agitation, thereby dispensing sodium bicarbonate or water to form a concentrated solution of sodium bicarbonate.

Even when the continuous dissolving apparatus of sodium bicarbonate as previously proposed is employed, however, the opening procedure of the vessel containing a necessary amount of sodium bicarbonate for one dialysis and the dosing operation into the storing tank such as a hopper communicating with the powder-feeding means are required. This variant is disadvantageous from the hygienic standpoint, because sodium bicarbonate and the storing tank are contacted with air for long periods of time. Further, there is no disclosure in the patent publication on the automatization and the labor saving for the washing and disinfecting operations of the powder-feeding means.

Accordingly, an object of the invention is to provide a hygienic and labor-saving dissolving apparatus of a powdery or granular, solid adjusting agent for a dialytic solution, which is obviates manual handling and dosing operations of vessels and the agent into a tank, which considerably curtails the time of direct contact of the adjusting agent with impure air, and which allows simple and convenient washing and disinfecting operations for the whole system in contact with a dissolved solution of the adjusting agent.

SUMMARY OF THE INVENTION

An apparatus for dissolving an adjusting agent of a dialytic solution according to the invention comprises a vessel containing sealingly a constant quantity of a powdery or granular solid adjusting agent of the dialytic solution, a feeding means of supplying a fluid for dissolving the adjusting agent to said vessel, and a dissolving tank for mixing and dissolving the adjusting agent with said fluid and for storing the mixed solution.

The dissolving apparatus described above, as one embodiment, comprises a vessel-holding means for supporting the vessel with the adjusting agent herein, a connecting means attached removably to a mouth of said vessel, a dissolving tank for mixing and dissolving said adjusting agent with water, a channel means of a recycling system communicating with an interior of said vessel through said connecting means and with said dissolving tank, a water-feeding means connected to said recycling system for feeding water, an agitator for agitating the mixed solution, and a discharging means for withdrawing the mixed solution from said dissolving tank.

As another embodiment, the dissolving apparatus according to the invention comprises a sealable dissolving tank, a water-feeding means for introducing a predetermined volume of water into said dissolving tank, a channel means of a recycling system for communicating said dissolving tank with said vessel, a pump unit for supplying water from the sealed dissolving tank through said channel means to the vessel to dissolve the adjusting agent therein and for recycling the mixed solution to said dissolving tank, and a discharge means for withdrawing the mixed solution from said dissolving tank.

In this embodiment, the connecting means may be provided integrally with an opening means for removing a sealing material from the sealed mouth of the vessel.

The apparatus according to the invention may be constructed in such a way that one of the channel means communicating the vessel with the dissolving tank is provided with an on-off valve, the water-feeding means being connected between said valve and the vessel for directly introducing water into said vessel, while the mixed solution of the adjusting agent with water flows into the dissolving tank through the other of the channel means communicating the vessel with the dissolving tank.

Further, the channel means of the recycling system, the water-feeding means or the dissolving tank may be provided with a means for feeding a washing or disinfecting solution.

Still further, the agitator may comprise a pump arranged in the channel of the recycling system for recycling the mixed solution hereto.

In this case, for mixing and dissolving the adjusting agent with water the apparatus may be provided with a means for detecting the end of mixing and dissolution, and a means (such as one utilizing the venturi principle) for returning residual liquid from the vessel to the dissolving tank after the mixing and dissolution has been completed.

The apparatus preferably includes a plurality of vessel-holding means each holding a vessel integrally mounted thereon, as well as a transfer unit for simultaneously and sequentially transferring the plurality of vessels kept by the vessel-holding means toward the connecting means. Alternatively, the plurality of vessel-holding means is moved individually and sequentially to transfer the vessels held by the plurality of the vessel-holding means toward the connecting means.

In practice of the invention, the vessel-holding means may be integrated with the connecting means.

The discharge means for withdrawing the mixed solution may be of any type provided that the solution within the dissolving tank and the recycling system can be discharged, and may be arranged in the dissolving tank or the channel means.

For preparing the dialytic solution using a plurality of the adjusting agents, on the other hand, a plurality of the apparatus according to the invention may be arranged in parallel for dissolving each adjusting agent individually in water and finally combining the plurality of solutions to form a mixed solution. Alternatively, a plurality of the apparatus according to the invention may be arranged in series, in the first apparatus of which the first agent is mixed with water and then transferred to the second apparatus for dissolving the second agent therein and so on to form the final mixed solution.

In accordance with the dissolving apparatus of the invention, a vessel containing sealingly a certain amount of the powdery or granular, solid adjusting agent for dialytic solution, as well as a dissolving tank therefor are provided, a certain quantity of fluid supplied by the fluid-feeding means is introduced into said vessel to dissolve the solid adjusting agent to form a mixed solution which is then stored in the dissolving tank for obtaining a determined concentration of the dissolved solution therein, and finally the resulting mixed solution may be discharged smoothly to the next step, such as an adjusting apparatus for the dialytic solution, through a delivery means.

Now, the invention will be described in more detail for its embodiments with reference to the accompanying drawings.

BRIEF DESCRIPTION OF THE DRAWINGS

FIGS. 4 and 5 illustrate an embodiment of a connecting means having the opening means used in the apparatus of FIG. 2, in which FIG. 4 is a sectional view of main portions while FIG. 5 is a broken perspective view of a cutter element of FIG. 4.

PREFERRED EMBODIMENTS OF THE INVENTION

Figure 1:
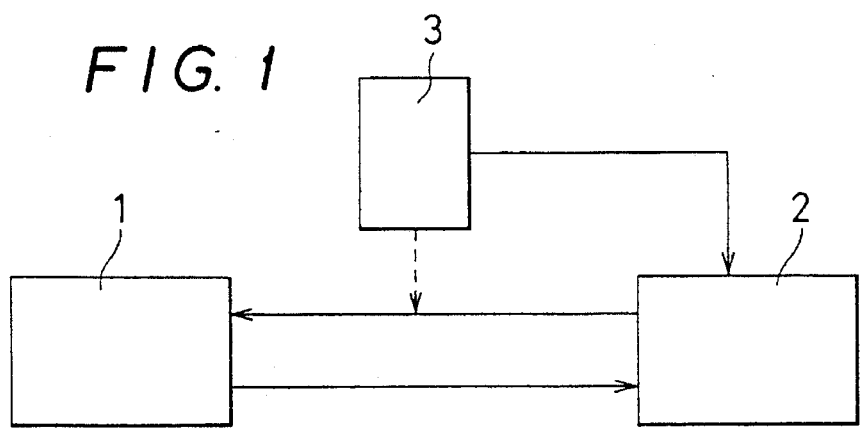
FIG. 1 is a schematic system diagram showing a basic principle of the dissolving apparatus for an adjusting agent of dialytic solution according to the invention.

Now, the principle of dissolving apparatus for an adjusting agent of dialytic solution according to the invention will be described in detail with reference to FIG. 1, in which numeral 1 represents a vessel containing sealingly a constant quantity of a powdery or granular, solid adjusting agent of dialytic solution while numeral 2 represents a dissolving tank for storing a mixed solution obtained by dissolving the solid adjusting agent. According to the invention, a fluid-feeding means 3 is provided in such a way that a dissolving fluid (water) is supplied to the solid adjusting agent within the vessel 1 to dissolve the same and then the resulting dissolved solution of the adjusting agent is stored in the dissolving tank 2 for mixing thereof. In this case, the vessel 1 and the dissolving tank 2 are communicate with each other to form a recycling system for the dissolved solution. For this purpose, the fluid-feeding means 3 is connected to the dissolving tank 2 for feeding a predetermined quantity of the dissolved solution thereto (a solid line) or is connected for directly feeding the dissolved solution to the vessel 1 (a broken line).

Thus, in accordance with the invention, for the dissolving tank of the prior art, means for feeding a constant quantity of the adjusting agent may be omitted so as to directly feed the dissolved solution to the vessel, while the adjusting agent within the vessel may be collected to obtain a mixed and dissolved solution of the adjusting agent conveniently and hygienically in a required concentration.

In the following, a preferred embodiment of the present apparatus based on such principle will be described in detail.

EXAMPLE 1

Figure 2:
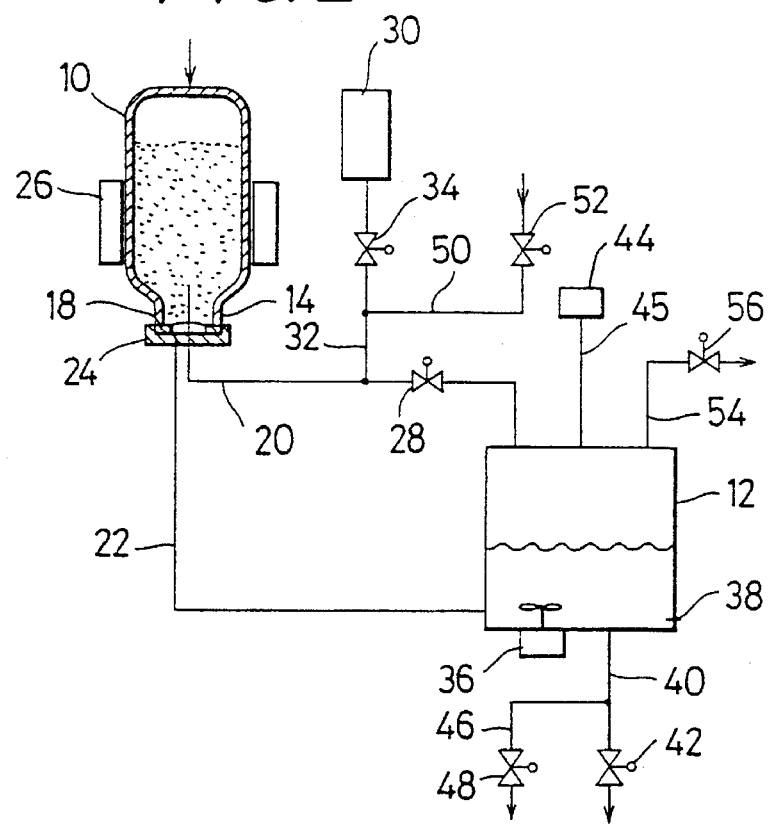
FIG. 2 is a schematic system diagram showing an embodiment of the dissolving apparatus according to the invention.
Figure 3:
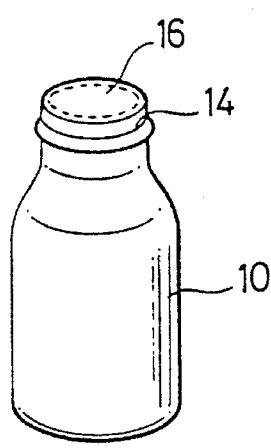
FIG. 3 is a perspective view of the vessel containing the adjusting agent used in the apparatus according to the invention.

FIG. 2 is a schematic system diagram showing the first embodiment of the dissolving apparatus according to the invention, in which a numeral 10 represents a vessel containing a solid adjusting agent while numeral 12 represents a dissolving tank for the adjusting agent. The vessel 10, as illustrated in FIG. 3, consists of a polyethylene container shaped by a blow molding procedure in the form of a cylinder. The vessel 10 at its circular mouth 14 is sealed by a polyethylene film 16 and contains sealingly therein a constant quantity of the solid adjusting agent. Then, the sealing film 16 of the vessel 10 is opened by a required opening means while the mouth 14 is provided air-tightly with a connecting element 24 for connecting pipes 20 and 22 communicating with the dissolving tank 12 optionally through a sealing element 18. In this case, the vessel 10 is inverted with its mouth 14 downward and kept by a vessel-holding element 26 at a higher level than the dissolving tank 12.

When the vessel 10 thus constructed is connected to the dissolving tank 12, one pipe 20 inserted through the connecting element 24 communicates through an on-off valve 28 with an upper portion of the dissolving tank 12 while the other pipe 22 is communicates with a lower portion of the tank 12. The one pipe 20 is provided between the vessel 10 and the valve 28 with a water-feeding pipe 32 connected to a water-supplying means 30 via an optional on-off valve 34. The dissolving tank 12 is provided at its bottom with an agitator 36 and with a level switch 38 for detecting a liquid level within the dissolving tank 12. Further, dissolving tank 12 is provided at its bottom with a discharging pipe 40 through an on-off valve 42 for discharging the mixed solution, while at its top is provided with an air-pipe 45 having an air-filter unit 44 and communicating with an atmosphere.

In this embodiment of the apparatus, a waste pipe 46 is branched through an on-off valve 48 from the discharging pipe 40 for disposing of an excess mixed solution. Further, an auxiliary feeding pipe 50 is branched through an on-off valve 52 from the water-feeding pipe 32 for introducing a washing or disinfecting liquid for the mixed solution system, while the dissolving tank 12 is provided with another auxiliary pipe 54 via an on-off valve 56 for discharging the washing or disinfecting liquid.

Next, operation of the apparatus of FIG. 2 will be described hereinbelow.

1. A Dissolving Step of the Adjusting Agent

At first, vessel 10 kept on the vessel-holding element 26 may be applied to this embodiment of the invention, either in its open state or in the case of providing an opening means for the connecting element 24 as described hereinafter.

When the on-off valve 34 of the water-feeding pipe 32 is opened, water supplied by the water-feeding means 30 flows through the pipe 20 into the vessel 10 and then through the pipe 22 into the dissolving tank together with the adjusting agent. At this point, a sufficient quantity of water is supplied in such a manner that a constant amount of the adjusting agent in the vessel 10 may be dissolved by water to give a predetermined concentration. Thus, by supplying such quantity of water, all of the adjusting agent within the vessel 10 may flow into the dissolving tank 12 together with water. After the predetermined quantity of water has been introduced, the valve 34 of the water-feeding pipe 32 is closed. In this case, it is desirable to use hot water in order to facilitate dissolution of the adjusting agent. Further, all remaining solution within the vessel 10 may flow into the dissolving tank with opening of the valve 28.

Then, in the dissolving tank 12 an agitator 36 is driven to mix the adjusting agent with water. The agitator 36 may be driven for a predetermined period of time or may be set for its driving by providing a detector (not shown) of concentration in the dissolving tank 12 for detecting the concentration of the mixed solution and its stable state.

After the adjusting agent is agitated and mixed with water in the dissolving tank 12 to form a concentrated solution of predetermined concentration, the on-off valve 42 is opened to transfer the concentrated solution from the dissolving tank 12 through the discharging pipe 40 to the next step, such as a unit for preparing a dialytic solution, and this charge pipe 40 may be provided with a pumping unit.

2. Washing and Disinfecting Steps

As described previously, after the predetermined amount of concentrated solution has been prepared to finish the dissolving step, the valve 42 of the discharging pipe 40 is closed while the on-off valve 48 of the waste pipe 46 is opened to dispose of all of the remaining solution left within the dissolving tank 12. After having finished the disposal, the valve 48 is closed while on-off valves 52 and 56 of auxiliary feeding and discharging pipes 50 and 54 are opened to introduce a washing liquid or a disinfecting liquid diluted in a certain concentration (for example, a diluted sodium hypochlorite solution) or hot water into the dissolving tank 12 containing the mixed solution of the adjusting agent via the used vessel 10. When a liquid-level in the dissolving tank 12 is increased thereby, the on-off valve 28 may be opened to fill the pipe 20 with the liquid and thus to wash or disinfect all of the dissolving and mixing systems. In this case, any excess liquid may overflow through the auxiliary discharging pipe 54 by opening the valve 56 and may be disposed of externally. For this purpose, the agitator 36 may be activated, if necessary. In order to perform the washing and disinfecting operation for the next step, the on-off valve 42 of the discharging pipe 40 may be opened to feed the washing or disinfecting liquid to the corresponding step. After the washing and disinfecting step is over in this way, the valve 48 of the waste pipe 46 is opened again to dispose of all remaining solution from the dissolving tank 12.

Figure 4:
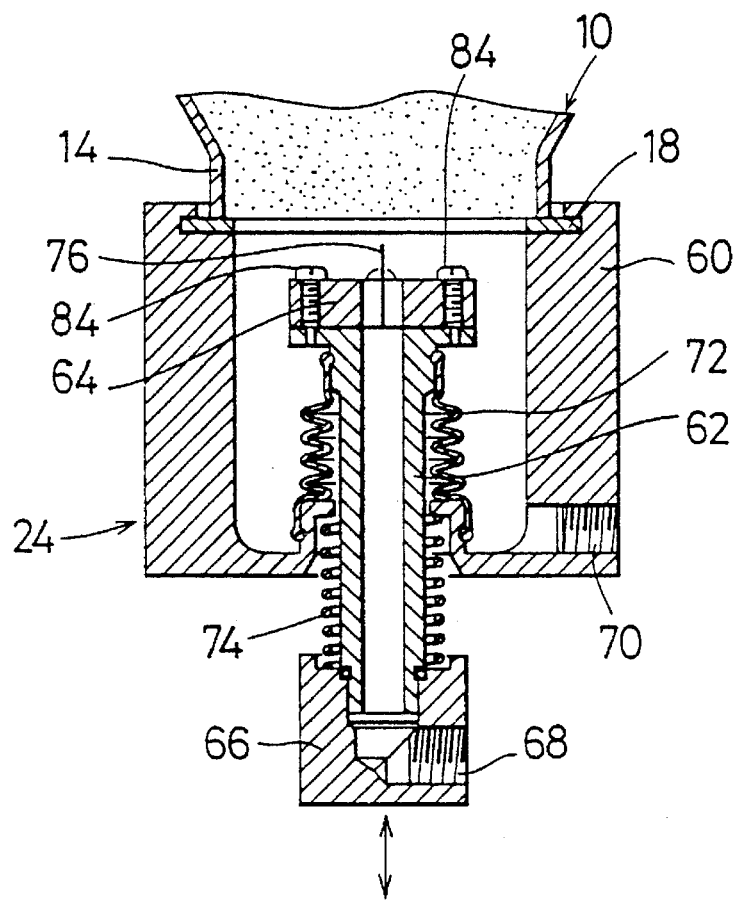
Figure 5:
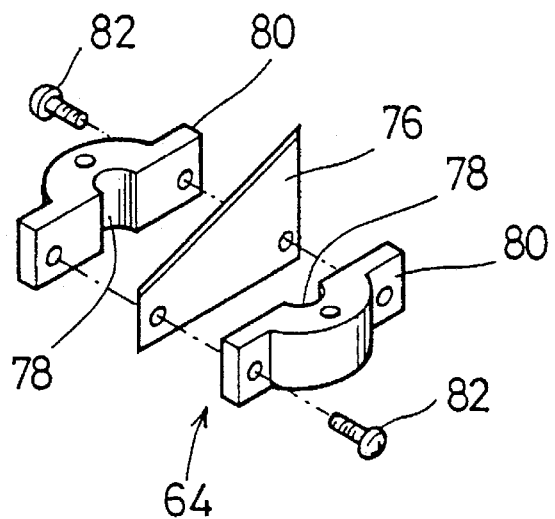

FIGS. 4 and 5 show one embodiment of the connecting element 24 with the opening means which may be applied to the vessel 10 used in the embodiment of FIG. 2.

Referring to FIG. 4, the connecting element 24 comprises a cylindrical casing 60 which at its one end is provided air-tightly through a sealing element 18 with a mouth 14 of the vessel 10 while a movable tube 62 is inserted through the other end. The movable tube 62 has a top end in the casing 60, which is provided with a cutter element 64. The movable tube 62 at its other end outside the housing 60 is connected to an adapter 66. The adapter 66 and the lower end of the casing 60 are provided with channels 68 and 70 for connecting the pipes 20 and 22, respectively (see FIG. 2). Further, the movable tube 62 is enclosed by a bellows 72 inside the casing 60 and is surrounded by a spring 74 outside the casing in order to permit axial and elastic movement thereof. With this opening means thus constructed, the movable tube 62 is urged against the spring 74 by an automatic urging mechanism to enter the casing 60, thereby allowing a cutter edge 76 of the cutter element 64 to tear a film 16 sealing the vessel 10 for achieving the automatic opening of the vessel 10. In order to construct the cutter element 64 of this embodiment, as illustrated in FIG. 5, the cutter edge 76 is sandwiched between symmetrical holding pieces 80, 80 each having at its center a groove 78, which pieces are connected to each other with screws 82, 82 and further secured to a front end of the movable tube 62 by other screws 84, 84. The connecting element 24 thus constructed allows the smooth feeding of water to the vessel 10 through a passage 68 of the movable tube 62, thereby causing the adjusting agent with water to flow from the vessel 10 into the dissolving tank 12 through a passage 70 of the casing 60 and a pipe system 22 (see FIG. 2).

EXAMPLE 2

Figure 6:
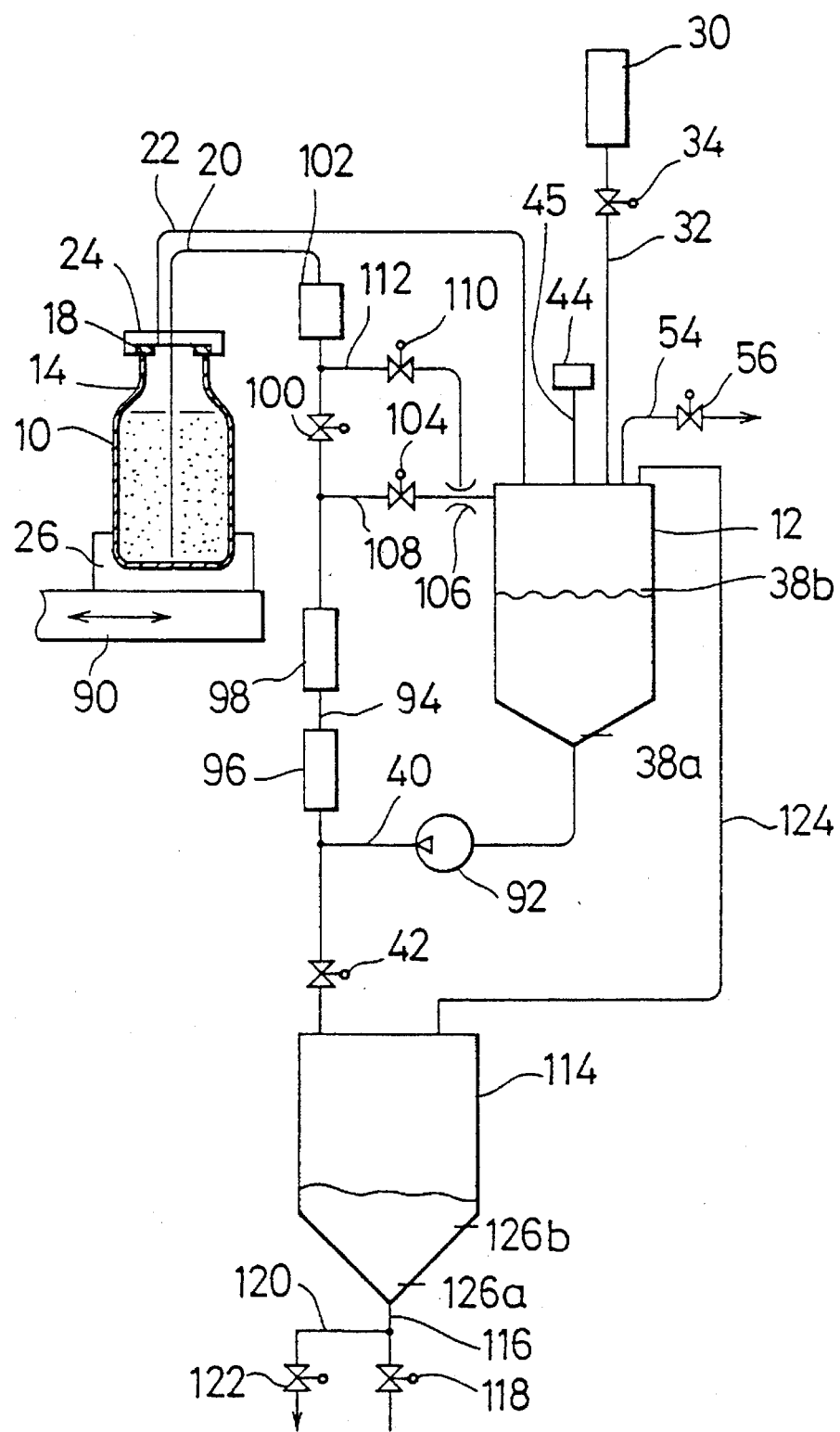
FIG. 6 is a schematic system diagram of another embodiment of the apparatus according to the invention.

FIG. 6 is schematic system diagram showing a second embodiment of the dissolving apparatus of the adjusting agent according to the invention, wherein the same references are used for the identical components in FIG. 2 unless otherwise indicated, for the purpose of convenient illustration.

More specifically, in the embodiment of FIG. 6, the vessel 10 is held in a normal state by the vessel-holding element 26 which in turn is movably mounted on a transferring unit 90. Further, in this embodiment a dissolving tank 12 at its top is connected to a water-feeding pipe 32 leading to a water-feeding means 30. A discharge pipe 40 from a bottom of the dissolving tank 12 is provided with a pumping unit 92 which on the downstream side is branched to form a branched pipe 94, which in turn communicates with a pipe 20 inserted through a connecting element 24 of the vessel 10. The branched pipe 94 and the pipe 20 are provided sequentially with a detector of concentration 96, a flow switch 98, an on-off valve 100 and a float switch 102. A connective portion of the float switch 102 with the valve 100 communicates with an upper portion of the dissolving tank 12 by a communicating pipe 108 through an on-off valve 104 and a venturi-tube 106. Further, the valve 100 with the float switch 102 is connected through an on-off valve 110 with a return pipe 112 communicating with a throat portion of the venturi-tube 106. To the discharging pipe 40 on its downstream side is connected through an on-off valve 42 a storing tank 114 which in turn at its bottom is connected to another discharge pipe 116 having an on-off valve 118 for discharging a stored solution while the discharging pipe 116 is branched to provide a waste pipe 120 through an on-off valve 122 for disposing of an excess of stored solution. Upper portions of the storing tank 114 and the dissolving tank 12 are connected to each other through a communicating pipe 124. The dissolving tank 12 is provided with a level-switch 38a for detecting a lower liquid level and another level-switch 38b for detecting a required constant level, while the storing tank 114 is also provided with a level-switch 126a for detecting a lower liquid level and another level-switch 126b for detecting a required constant level.

Now, operation of the dissolving apparatus of FIG. 6 will be described hereinbelow.

1. A Dissolving Step for the Adjusting Agent

Also in this embodiment, the vessel 10 retained by the vessel-holding element 26 may be applied either when it has previously been opened or when the connecting element 24 has been provided with an opening means, as described hereinafter.

At first when the on-off valve 34 of the water-feeding pipe 32 alone is opened, water supplied from the water-feeding means 30 flows into the dissolving tank 12. With water reaching a required level in the dissolving tank 12, the level-switch 38b detects the level to close the on-off valve 34, thereby terminating the water-feeding. Then, opening of the on-off valve 100 allows the pumping unit 92 to start driving. Thus, water in the dissolving tank 12 flows through the discharge pipe 40, the branched pipe 94 and the pipe 20 into the vessel 10. At this point, the constant amount of the adjusting agent sealed within the vessel 10 returns together with water to the dissolving tank 12 through the pipe 22. Then, by operating the pumping unit 92 continuously, the solution in the dissolving tank 12 may recycle through the vessel 10 and allow for mixing and dissolving the adjusting agent in the tank 12. In this embodiment, the mixing and dissolving procedure may be achieved without an agitator in the dissolving tank 12. For this purpose, a concentration of the mixed solution may be detected by the concentration detector 96. Upon establishing the required concentration, the on-off valve 100 is closed while the on-off valve 104 is opened. In this embodiment, in order to recycle the solution in the dissolving tank 12 through the vessel 10 and allow the adjusting agent to flow out of the vessel 10 it is necessary to utilize a flow rate of the recycling solution over a required rate, so that such flow rate is detected by the flow switch 98 arranged in the branched pipe 94, which may generate a warning signal upon a lower rate than the present requisite flow rate. When the valve 100 is closed and the valve 104 is opened as described above, the solution in the dissolving tank 12 may recycle through the branched pipe 94 and the communicating pipe 108. At this point, by an effect of the venturi-tube 106 (Bernoulli's theorem) provided for the communicating pipe 108 the return pipe 112 connected to the throat portion of the venturi-tube 106 may generate a negative pressure. If the on-off valve 110 on the return pipe 112 is opened at this moment, the remaining solution in the vessel 10 may return to the dissolving tank through the pipe 20 and the return pipe 112, thereby actuating the float switch 102. After a certain period of time, the valves 104 and 110 are closed while the pumping unit 92 is shut off, resulting in termination of the mixing and dissolution of the adjusting agent of the dissolving tank 12.

After the concentrated solution of a desired concentration has been prepared in the dissolving tank 12, the solution is transferred from the dissolving tank 12 to the storing tank 114 when the stored solution in the storing tank 114 is discharged and the level-switch 126b detects its level therein. At this moment, the pumping unit 92 may optionally be driven to shorten the transporting time. After the level of the dissolving tank 12 is lowered and the level-switch 38a detects the level therein, the on-off valve 42 is closed to terminate the feeding of the solution after a predetermined time which has been previously set for transferring all solution from the dissolving tank 12 to the storing tank 114. In this way, the concentrated solution in the storing tank 114 may be transferred to the next step of the present apparatus through the discharge pipe 116.

2. A Washing and Disinfecting Step

As described above, after the required amount of the concentrated solution has been prepared in the dissolving tank 12 and then transferred to the storing tank 114, the valve 118 of the discharge pipe 116 is closed and the valve 122 of the waste pipe 120 is opened to dispose of the remaining concentrated solution from the storing tank 114. After completing the disposal, the valve 122 is closed and the on-off valve 118 of the discharge pipe 116 is opened to a washing liquid or a disinfecting liquid diluted to a desired concentration (a diluted sodium hypochlorite solution) or hot water is introduced into the storing tank 114 from the adjusting apparatus through the discharge pipe 116. Then, the washing or disinfecting liquid supplied into the storing tank 114 is fed to the dissolving tank 12 through the communicating pipe 124. An excess amount of the liquid in the dissolving tank 12 is overflows through the auxiliary pipe 54 by opening the valve 56 and is discharged externally. After the feeding of the washing and disinfecting liquid to the snoring and dissolving tank 114 and 12 has been completed, the valve 118 is closed to terminate the feeding of the washing and disinfecting liquid. Thereafter, the pumping unit 92 is driven and the valves 100, 104, 110 and 42 are optionally opened to wash and disinfect all the system for the mixed solution of the adjusting agent. When the washing/disinfecting step is completed, the on-off valve 42 and 122 are opened to dispose of the remaining liquid from the dissolving and storing tank 12 and 114.

Figure 7:
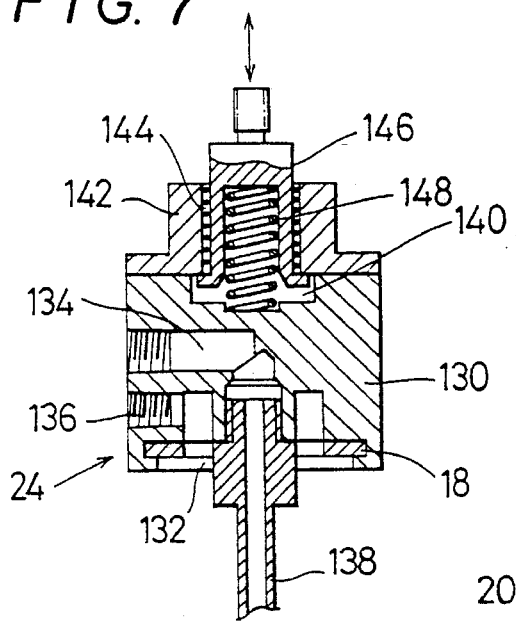
FIG. 7 is a sectional view of main portions showing an embodiment of the connecting means having the opening means used in the apparatus of FIG. 6.

FIG. 7 show an embodiment of the connecting element 24 applicable to the vessel which is employed for the apparatus of FIG. 6.

With referring to FIG. 7, a connecting element 24 is constructed in such a way that a main body 130 at its bottom is provided with a recess 132 fitting to a mouth 14 of the vessel 10, a portion of which recess is provided with a sealing element 18 (see FIG. 6). Further, the recess 132 at its center and its circumference is provided with separate channels 134, 136 for connecting pipes 20, 22 (see FIG. 6), respectively. To the one channel 134 is connected an extension pipe 138 which may sufficiently be inserted into the vessel 10. The main body 130 is provided with a recess 140 at its center top and securely with a flange element 142, into which at its center is inserted a vertically movable spring housing 146 through a bearing 144. Within the spring housing 146 is arranged a spring 148, one end of which is urged against the recess 140 of the main body 130. If the spring housing 146 thus constructed is pushed from the above, the main body 130 of the connecting element 24 may be urged against the mouth 14 of the vessel 10 under the elastic action of the spring 148 to achieve a leak-free air-tight fitting. In order to provide the connecting element 24 of this embodiment with an opening means, for example, a top end of the extension pipe 138 may be fabricated to have a sharp edge or a cutter.

EXAMPLE 3

Figure 8:
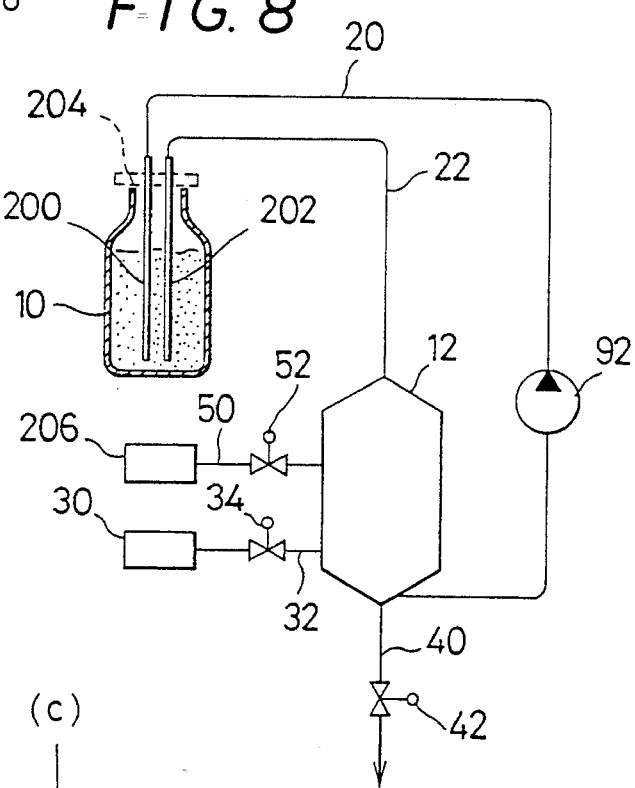
FIG. 8 is a schematic system diagram showing a further embodiment of the apparatus according to the invention.

FIG. 8 is a schematic system diagram showing a third embodiment of the dissolving apparatus for the adjusting agent according to the invention, wherein the same references are used as in FIG. 2 for identical components for convenient illustration unless otherwise indicated.

In the embodiment of FIG. 8, a dissolving tank 12 is of a closable construction, in which the vessel 10 is arranged above a storing level of the dissolving tank 12. As in the previous embodiment, the vessel 10 may be retained by a vessel-holding element 26. In order to communicate the dissolving tank 12 with the vessel 10 there are arranged pipes 20 and 22, of which connecting ends are connected to extension pipes 200 and 202 fully extended into the vessel, namely to a bottom of the vessel 10. In this case, front ends of these pipes 20 and 22 may be extended directly into the vessel 10. Thus, one of the pipes 20 communicating the dissolving tank 12 with the vessel 10 is connected to the pumping unit 92, thereby constructing a recycling system for recycling the stored water of the dissolving tank through the vessel. For this embodiment, it is not necessary to connect a connecting element through a sealing material to the mouth of the vessel as in the previous embodiments, but it is preferable to provide a covering 204 as a dust-protective means for covering the mouth, if required.

To the dissolving tank 12 is connected the water-feeding pipe 32 leading to the water-feeding means 30 via an on-off valve 34. Further, the dissolving tank 12 at its bottom is provided with a discharge pipe 40 through an on-off valve 42 for discharging the mixed and dissolved solution. To a portion of the dissolving tank 12 is connected an auxiliary feeding means 206 by an auxiliary feeding pipe 50 through an on-off valve 52 for supplying the washing and disinfecting liquid to the system of the mixed solution.

Next, operation of the dissolving apparatus of FIG. 8 will be described hereinbelow.

1. A Dissolving Step of the Adjusting Agent for Dialytic Solution

At first, the valve 34 is opened for the water-feeding means 30 to introduce a constant quantity of water into the dissolving tank 12. In this case, a feeding volume of water is set larger than that of the dissolving tank 12, so that water filling the dissolving tank 12 and overflowing therefrom flows through the pipe 22 and the extension pipe 202 into the vessel 10 to increase a level within the vessel 10 above a lower opening of the extension pipes 200 and 202 (for example, half of the height of the vessel 10). If the feeding volume of water is set in such a manner, the dissolving tank 12, the pipe 22 and the extension pipe 202 may be air-free therein. When the dissolving tank 12 is closed and the pumping unit 92 is driven in such state, a negative pressure may be generated on the upstream side of the pumping unit 92 (within the pipe 22). As a result, the solid adjusting agent in the vessel 10 may be sucked together with water from the lower opening of the extension pipe 202. Then, the pumping unit 92 is driven continuously to collect the adjusting agent together with water under mixing into the dissolving tank 12, thus constructing the recycling system.

As in the second embodiment, the required concentration of the solution may be prepared within the dissolving tank 12.

The concentrated solution prepared in the dissolving tank 12 is then transferred through the discharge pipe 40 to the next step by opening the valve 42. The solution in the vessel 10 may be recovered automatically by a syphon effect into the dissolving tank 12.

2. A Washing and Disinfecting Step

As described previously, after the concentrated solution of the desired concentration has been prepared and the required dissolving step has been completed, the remaining solution in the dissolving tank 12, if any, is discharged through the discharge pipe 40 by opening the valve 42. Upon finishing the discharging procedure, the valve 42 is closed and then the valve 52 of the auxiliary feeding pipe 50 is opened to feed a washing liquid or a disinfecting liquid diluted to a desired concentration (for example, a diluted sodium hypochlorite solution) or hot water into the mixing and dissolving system through the dissolving tank 12, as for the water-feeding in the dissolving step. In this case, the pumping unit 92 may be driven to wash and disinfect the entire system of mixing solution. After the washing and disinfecting step, the on-off valve 42 is opened to dispose of all remaining liquid through the discharge pipe 40 from the dissolving tank 12 and the entire dissolving system.

Continuous Use of Vessels Each Containing the Adjusting Agent

According to each of the embodiments described above, a single vessel 10 containing the adjusting agent has been described but a plurality of vessels each containing the adjusting agent may be continuously utilized in these embodiments.

Figure 9:
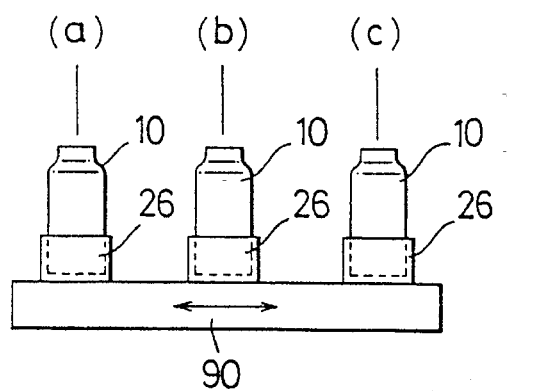
FIG. 9 is a schematic view showing arrangement of a transferring unit and a plurality of the vessels each containing the adjusting agent suitable for continuous use in the apparatus according to the invention.

For example, as illustrated in FIG. 9 corresponding to the second embodiment, a plurality of vessel-holding elements 26 are placed on a transferring unit 90, each of said elements carrying each vessel 10 and being sequentially transferred to a predetermined position of a connecting element 24. In FIG. 9, the vessels 10 are positioned at sites (a), (b) and (c), respectively, and joined to the connecting element 24 at the site (c) for feeding water, for example. Unless the connecting element 24 is provided with an opening means, a required opening means may open the vessel 10 at the site (b) when the vessel 10 is moving from the site (b) to (c). The site (b) is provided with a proximity switch in the vicinity of the vessel 10, which detects the presence of the adjusting agent in the vessel 10 and the presence of the vessel 10 per se. When the adjusting agent or the vessel 10 is not present, the transferring unit 90 is operated without the opening procedure in order to transfer the next vessel 10 now on the site (a) into the site (b) for performing the detection of that vessel 10 again. As to the number of the vessels used for a single mixing and dissolving procedure of the adjusting agent, optionally a setting device may be provided for controlling the transferring unit 90 and the opening means. Further, a transferring mechanism of the transferring unit 90 may be of a slide or turntable type.

Use of a Washing and Disinfecting Container

In each of the previous embodiments, the washing and disinfecting procedure is carried out in the state of connecting a consumed vessel 10, but an exclusive container may be utilized for the washing and disinfecting operation in order to facilitate replacement of the vessel 10.

In case the washing with water is employed without using the washing and disinfecting liquid, water may be supplied to the mixing and dissolving system through the water-feeding means in each of the above embodiments.

Use as the Adjusting Apparatus of the Dialytic Solution

In each of the embodiments, a known type of temperature-controlling-, deaerating-, concentration-detecting- or other function may be added to the adjusting apparatus for providing a concentration of the solution in the dissolving tank 12 corresponding to the dialytic solution, thereby allowing the apparatus of the present invention to be used directly as the adjusting apparatus of the dialytic solution.

Simultaneous Use of a Plurality of Vessels Containing Different Types of the Adjusting Agent In each of the above embodiments as described for preparing the dialytic solution of sodium bicarbonate system, for example, when two types of the adjusting agents are used, two lines of the mixing and dissolving systems corresponding to the vessels each containing the adjusting agent may be employed for convenience. Further, as a convenient means, each of two vessels may be provided with each of the containing elements which are connected in cascade to a pipe communicating the dissolving tank for sequentially feeding water to said two vessels in order to perform the simultaneous mixing and dissolution of said two types of the adjusting agents with water. Further, a switching valve may be arranged in a connecting portion of the pipe to the connecting elements for said two vessels in order to perform the simultaneous mixing and dissolution of said two types of the adjusting agents with water. Further, a switching valve may be arranged in a connecting portion of the pipe to the connecting elements for said two vessels in such a way that the adjusting agent in one of the vessels is at first dissolved in water and then the switching valve is switched and finally the adjusting agent of the other vessel is dissolved for mixing.

Although the sealing means of the vessel having a film attached to its mouth portion has been described for the apparatus according to the invention, the vessel is provided at a circumference of the mouth thereof with a thread, onto which a cap may be conveniently screwed to form the sealing means. Alternatively, a flexible vessel having a sealable mouth may be suitably employed, as well.

It will be appreciated from the various embodiments as described above that an automatic dissolving procedure may be achieved in accordance with the invention merely by placing in position the vessel containing adjusting agent. Thus, manual operations, such as opening of the vessel and dosing of the adjusting agent, as in the prior art may be avoided, resulting in very short contacting time of the adjusting agent with the atmosphere and hence very hygienic dissolution of the adjusting agent.

Particularly, the present apparatus may be effectively employed as a means for feeding the adjusting agent in the form of solution to the adjusting apparatus. Further, it may be utilized for the adjusting function, namely a main function of the adjusting apparatus for dialytic solution.

According to the second embodiment, without dissolving at one time all of the solid adjusting agent to be used prior to the start of dialysis, the solid agent may be dissolved during the dialytic procedure depending on a rate of consumption of the agent contained in each vessel, thereby feeding the dialytic solution to a plurality of units for dialysis. In this case, the dissolved and mixed solution may be a concentrated solution for minimizing volumes of the dissolving and storing tanks. Further, the present apparatus may be combined with a widely used popular adjusting apparatus for the dialytic solution.

Having illustrated and described the principles of the invention in the preferred embodiments, it should be readily apparent to those skilled in the art that the invention can be modified in arrangement and detail without departing from the spirit and scope of the invention.

What is claimed is:

1. Apparatus for dissolving an adjusting agent of a dialytic solution, comprising a vessel containing dry particulate adjusting agent for a dialytic solution, a dissolving tank, a first pipe communicating between a lower portion of said vessel and an upper portion of said dissolving tank, valve means in said first pipe, a second pipe communicating between a lower portion of said vessel and a lower portion of said dissolving tank, water supplying means connected to said first pipe, valve means for controlling the flow of water from said water supplying means to said first pipe, an agitator in a lower portion of said dissolving tank, a liquid level switch in said dissolving tank for detecting a liquid level within said dissolving tank, a third pipe connected with a lower portion of said dissolving tank for discharging liquid from said dissolving tank, valve means in said third pipe controlling the discharge of liquid from said dissolving tank through said third pipe, and sealing means by which said first and second pipes are sealingly connected to the lowest portion of said vessel, said vessel being at a higher level than said dissolving tank, whereby when said valve means in said first pipe is opened, all remaining solution within said vessel flows into said dissolving tank.

2. Apparatus for dissolving an adjusting agent of a dialytic solution, comprising a vessel containing dry particulate adjusting agent for a dialytic solution, a dissolving tank, a first pipe communicating between a lower portion of said vessel and an upper portion of said dissolving tank, valve means in said first pipe, a second pipe communicating between a lower portion of said vessel and a lower portion of said dissolving tank, water supplying means connected to said first pipe, valve means for controlling the flow of water from said water supplying means to said first pipe, an agitator in a lower portion of said dissolving tank, a liquid level switch in said dissolving tank for detecting a liquid level within said dissolving tank, a third pipe connected with a lower portion of said dissolving tank for discharging liquid from said dissolving tank, and valve means in said third pipe controlling the discharge of liquid from said dissolving tank through said third pipe, said first and second pipes communicating with said lower portion of said vessel by passing through the lowest portion of said vessel, said vessel being at a higher level than said dissolving tank, whereby when said valve means in said first pipe is opened, all remaining solution within said vessel flows into said dissolving tank.

* * * * *